US00PP17525P3

(12) United States Plant Patent
Meilan et al.

(10) Patent No.: US PP17,525 P3
(45) Date of Patent: Mar. 27, 2007

(54) POPLAR TREE NAMED 'CURLY POPLAR'

(50) Latin Name: *Populus canescans×Populus alba hybrid*
Varietal Denomination: Curly Poplar

(75) Inventors: Richard Meilan, West Lafayette, IN (US); Samuel Grober, Evanston, IL (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/111,700

(22) Filed: Apr. 22, 2005

(65) Prior Publication Data

US 2006/0242742 P1 Oct. 26, 2006

(51) Int. Cl.
*A01H 5/00* (2006.01)

(52) U.S. Cl. ..... Plt./218
(58) Field of Classification Search ..... Plt./218
See application file for complete search history.

*Primary Examiner*—Kent Bell
(74) *Attorney, Agent, or Firm*—Bose McKinney & Evans LLP

(57) ABSTRACT

A popular tree particularly distinguished by having highly figured wood is disclosed.

2 Drawing Sheets

Genus and species: *Populus canescans×Populus alba* hybrid.
Variety denomination: 'Curly Poplar'.

BACKGROUND OF THE NEW PLANT

The present invention comprises a new and distinct cultivar of poplar, botanically known as *Populus canescans×Populus alba* hybrid, and hereinafter referred to by the cultivar name 'Curly Poplar'. This tree was discovered as a naturally occurring mutated sprout of an unnamed, unpatented poplar tree that grew in a cultivated area in Maryland. This tree produces high value curly-figured veneer. This new tree is currently growing in a cultivated area (a front yard) in Evanston, Ill. 'Curly Poplar' has been asexually reproduced by vegetative cuttings and has been shown to reproduce true to type in successive generations of asexual propagation.

DESCRIPTION OF THE PHOTOGRAPHS

This new poplar tree is illustrated by the accompanying photographs which shows the tree's distinctive wood, a leaf from the tree and the overall habit of the tree. The colors shown are as true as can be reasonably obtained by conventional photographic procedures.

DESCRIPTION OF THE NEW CULTIVAR

Figure 1:
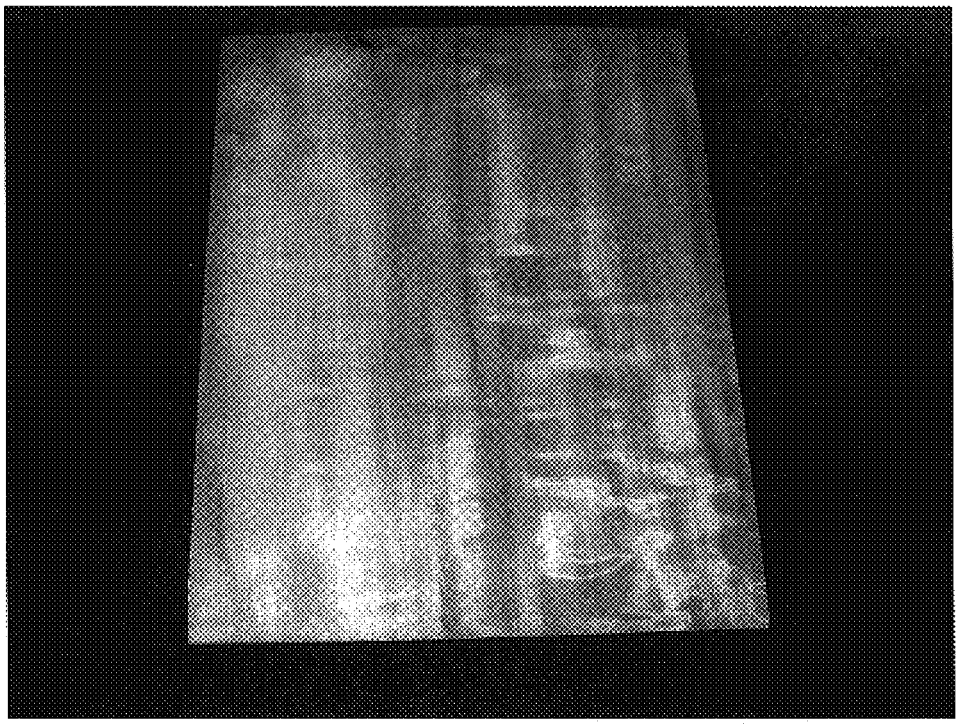
FIG. 1 shows the distinctive wood of the new poplar tree.
Figure 2:
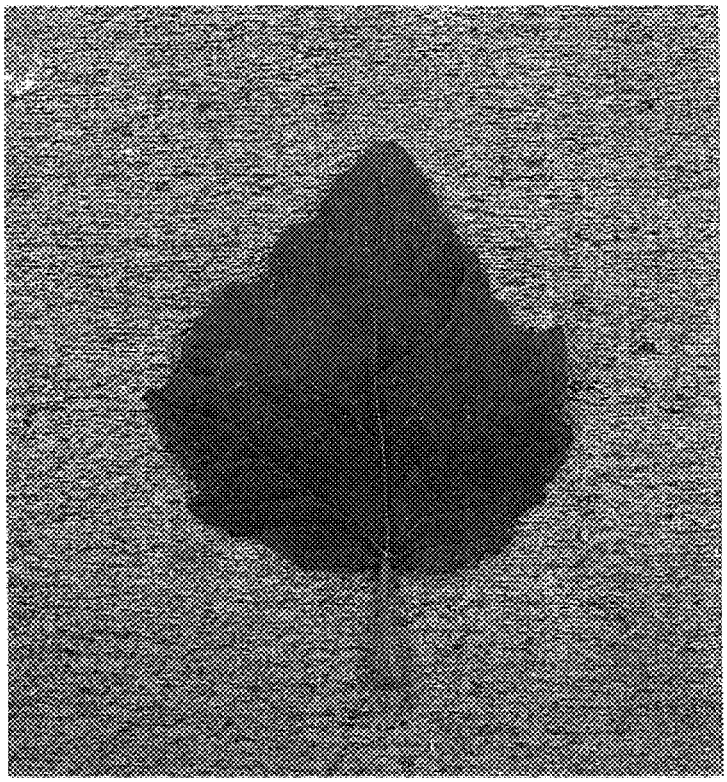
FIG. 2 shows a mature leaf from the tree.
Figure 3:
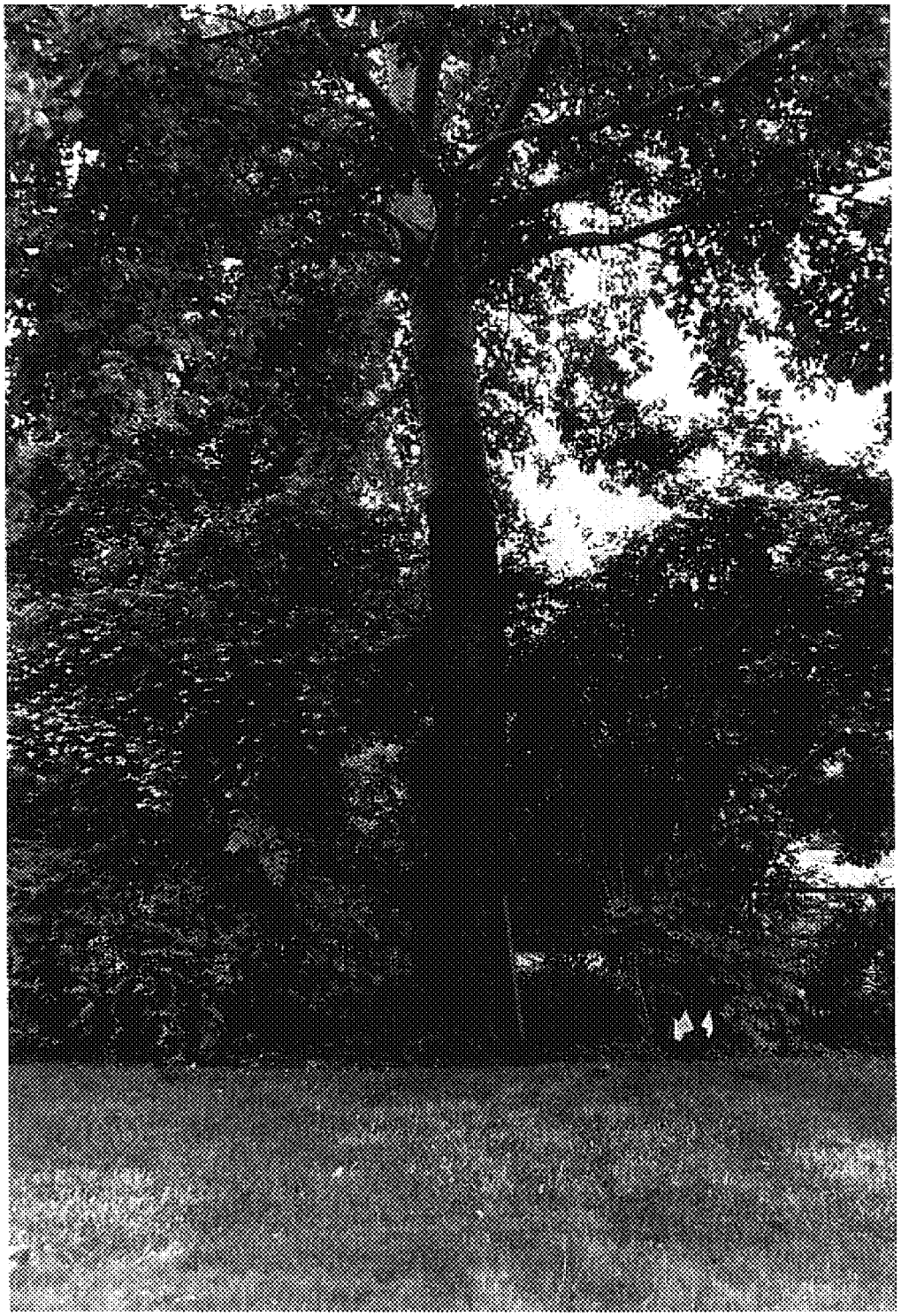
FIG. 3 shows the overall habit of the tree.

The following detailed description sets forth the distinctive characteristics of 'Curly Poplar'. The data which define these characteristics were collected from a 23-year-old tree in Evanston, Ill. Color references are to the Munsell Color Charts for Plant Tissues.

DETAILED BOTANICAL DESCRIPTION

Classification:
*Botanical name.*—*Populus canescans×Populus alba* hybrid.
*Common name.*—Poplar.

Tree:
*Shape.*—Upright and rounded with a dominant main trunk.
*Height (of entire tree including crown).*—Approximately 65 feet.

Trunk:
*Size, at 23 years of age.*—Average diameter: 23 inches, measured at 4.5 feet above the ground. Height (to first limb/branch): 15 feet.
*Growth habit.*—Erect excurrent branching.
*Growth rate.*—3 feet/year.
*Bark color.*—Mottled with 2.5Y 5/2 and 2.5Y 7/2.
*Bark texture.*—Medium with interlocking furrows.

Branches:
*Size.*—Crown diameter of tree 23.0 feet at 23 years. Branches aged 15 years: Length: 12 feet. Diameter: 5 inches.
*Branching habit.*—Dominant main stem with ascending excurrent branching.
*Color.*—2.5Y 8/4.
*Crotch angle.*—40 to 45 degrees.
*Internode length.*—Variable, from 6 inches to 3 feet.

Lenticels:
*Size.*—Length: ¼ inch. Width: ⅜ inch.
*Color.*—10R 6/8.
*Quantity.*—Approximately 2 to 3 per square inch.

Leaves:
*Immature.*—Length: 3–4 inches. Width: 2.5–4 inches. Shape: Sub-orbicular to deltoid, 3 poorly defined lobes. Apex: Acute to acuminate. Base: Truncate. Margin: Irregularly sharply dentate. Color: Upper surface: 2.5G 5.5. Lower surface: 5BG 4/4. Texture: Loose.
*Mature.*—Length: 2.5–3.5 inches. Width: 2–2.5 inches. Shape: Ovate. Apex: Acute to acuminate. Base: Truncate. Margin: Crenate-dentate. Texture: Firm. Color: Upper surface: 2.5G 5/8. Lower surface: 2.5G 8/4.
*Pubescence distribution.*—Lower surface.
*Pubescence color.*—5BG 4/4.

*Petiole length.*—1.75–2.5 inches.
*Petiole diameter.*—1/16 inch.
*Petiole color.*—5BG 4/4.
*Venation.*—Pinnate.

Leaf buds:
*Shape.*—Narrow-ovate.
*Length.*—3/8–1/2 inch.
*Width.*—1/8–3/16 inch.
*Pubescence.*—Light.
*Pubescence color.*—5YR 5/4.
*Bud scales.*—Size: Length: 3/8 inch. Diameter: 1/4 inch. Shape: Ovate. Number: 8.

Flower buds:
*Shape.*—Ovate-globose.
*Length.*—3/8–1/2 inch.
*Width.*—1/4 inch.
*Texture.*—Smooth.
*Color.*—7.5YR 5/4.

Flowers:
*Type.*—Dioecious male.
*Time of flowering.*—Early –mid-April.
*Length of flowering period.*—1 week.
*Size.*—Length: 2–4 inches. Diameter: 3/8–1/2 inch.
*Filament color.*—White.
*Anther color.*—Dark amber.
*Stamen number.*—8 to 12.

Disease and insect resistance: Resistant to anaerobic bacterial infection. No known insect pests.

COMPARISON WITH MOST SIMILAR CULTIVAR

The inventors do not know whether the parent tree still exists, therefor, no comparison can be made. However, when compared to other typical poplar trees. 'Curly Poplar' is a distinct variety of poplar due to its highly figured wood. The highly figured wood is due to the tree's undulating cross grain which results in a strong mottle-figured grain. All the other characteristics of this poplar tree are similar to those of *Populus canescans* and *Populus alba*.

'Curly Poplar' differs from the commercial variety 'Gnarly Poplar' (U.S. Plant Pat. No. 15,613) in that the overall shape of 'Curly Poplar' is upright and rounded, while the overall shape of 'Gnarly Poplar' is upright and ellipsoidal. The bark texture of 'Curly Poplar' is medium with interlocking furrows, while the bark texture of 'Gnarly Poplar' is smooth. Additionally, 'Curly Poplar' has a mature height of approximately 65 feet, while 'Gnarly Poplar' has an expected mature height of 30 to 45 feet.

'Curly Poplar' differs from the commercial variety 'Shinsei' (U.S. Plant Pat. No. 14,664) in that the overall shape of 'Curly Poplar' is upright and rounded, while the overall shape of 'Shinsei' is straight and narrow. The leaf bud length of 'Curly Poplar' ranges from 0.375 to 0.5 inches, while the leaf bud length of 'Shinsei' ranges from 0.79 to 0.98 inches.

We claim:

1. A new and distinct poplar tree as shown and described herein.

* * * * *